US012685797B1

(12) United States Patent
Landers

(10) Patent No.: US 12,685,797 B1
(45) Date of Patent: Jul. 21, 2026

(54) SYSTEMS AND METHODS OF TARGETED ENTITY DEGREDATION

(71) Applicant: Phillip G. Landers, Sanford, FL (US)

(72) Inventor: Phillip G. Landers, Sanford, FL (US)

( * ) Notice: Subject to any disclaimer, the term of this patent is extended or adjusted under 35 U.S.C. 154(b) by 0 days.

(21) Appl. No.: 19/012,816

(22) Filed: Jan. 7, 2025

Related U.S. Application Data

(63) Continuation-in-part of application No. 17/397,247, filed on Aug. 9, 2021, now Pat. No. 12,186,741.

(60) Provisional application No. 63/062,644, filed on Aug. 7, 2020.

(51) Int. Cl.

| | |
|---|---|
| *A61L 9/22* | (2006.01) |
| *A61L 2/02* | (2026.01) |
| *A61L 2/26* | (2006.01) |
| *A61L 101/50* | (2006.01) |
| *A61L 103/05* | (2026.01) |
| *A61N 1/40* | (2006.01) |
| *C02F 1/46* | (2023.01) |
| *C02F 101/36* | (2006.01) |
| *C02F 103/00* | (2006.01) |

(52) U.S. Cl.
CPC *A61L 9/22* (2013.01); *A61L 2/02* (2013.01); *A61L 2/26* (2013.01); *A61N 1/403* (2013.01); *C02F 1/4606* (2013.01); *C02F 1/4608* (2013.01); *A61L 2101/50* (2020.08); *A61L 2103/05* (2026.01); *A61L 2202/11* (2013.01); *C02F 2101/36* (2013.01); *C02F 2103/007* (2013.01); *C02F 2303/04* (2013.01)

(58) Field of Classification Search
CPC . A61L 9/22; A61L 2/0011; A61L 2/26; A61L 2101/50; A61L 2202/11; A61N 1/403; C02F 1/4606; C02F 1/4608; C02F 2101/36; C02F 2103/007; C02F 2303/04
See application file for complete search history.

(56) References Cited

U.S. PATENT DOCUMENTS

| | | | |
|---|---|---|---|
| 4,905,441 | A | 3/1990 | Landers |
| 6,596,204 | B1 | 7/2003 | Landers |
| 10,045,528 | B1 | 8/2018 | Landers |
| 2021/0351409 | A1* | 11/2021 | Lu ............... H01M 4/38 |

OTHER PUBLICATIONS

Jiang, S., Ma, A., 7 Ramachandran, S. (2018). "Negatove Air Ions and their Effects on Human Health and Air Quality Improvement," International Journal of Molecular Sciences. doi: 10.3390/ijms19102966.

* cited by examiner

*Primary Examiner* — Brendan A Hensel
(74) *Attorney, Agent, or Firm* — Terry M. Sanks, Esq.; Beusse Sanks, PLLC

(57) ABSTRACT

Systems and methods for reducing, destroying, or otherwise facilitating degradation of one or more targeted entities is disclosed. The method includes forming anionic polymer encapsulants (CAPs) including ingredients in a plasma reaction chamber (PRC). The ingredients include at least one of: a) one or more essential oils; and b) an energy amplifying liquid. The method includes creating a plasma gas in the plasma reaction chamber, in response to a pulsed electromagnetic energy field, and forming cold plasma by discharging dielectric barrier plasma discharges from the plasma reaction chamber into a fluid medium having one or more targeted entities dispersed therein. The system includes the components that facilitate the method as indicated.

10 Claims, 5 Drawing Sheets

300A
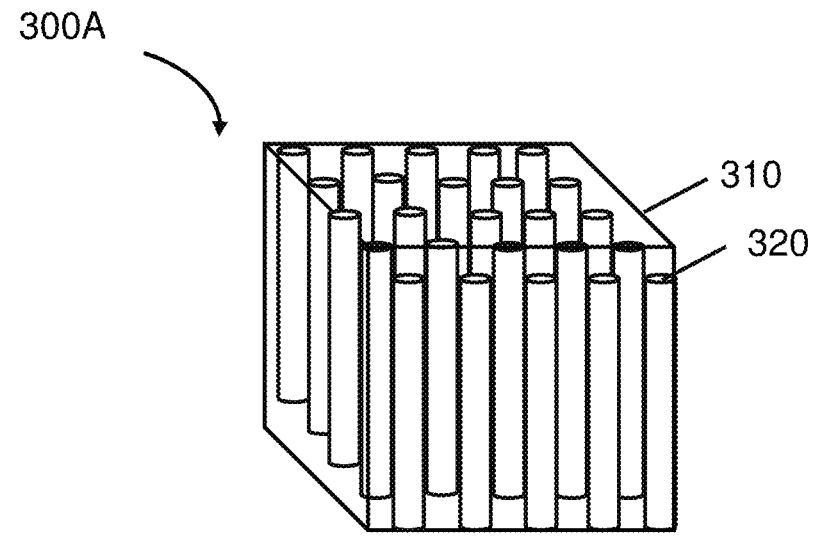
310
320
FIG. 3A
300B
300A
340    345
325
310
320
200
325
FIG. 3B
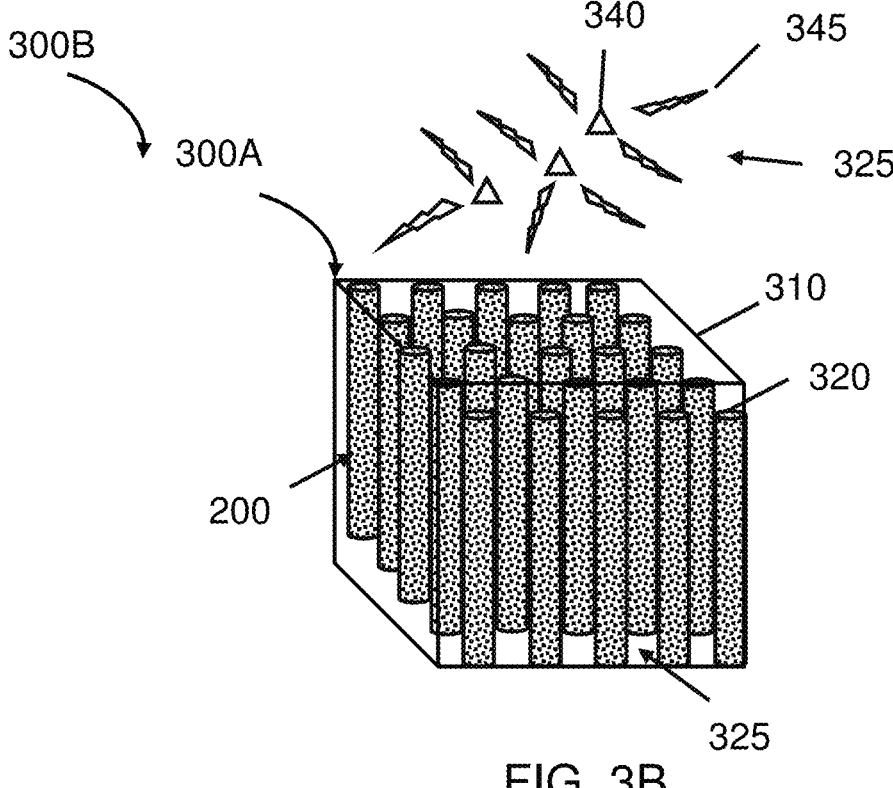

505

510

SYSTEMS AND METHODS OF TARGETED ENTITY DEGREDATION

CROSS REFERENCE TO RELATED APPLICATION

This application is a Continuation-In-Part of U.S. application Ser. No. 17/397,247, now U.S. Pat. No. 12,186,741 issued Jan. 7, 2025, which claims the benefit of U.S. Provisional Application No. 63/062,644 filed Aug. 7, 2020, incorporated herein by reference in their entirety.

FIELD OF THE INVENTION

This disclosure relates to a system and method of targeted entity degradation, such as, but not limited to, for example, destroying pathogens by using a negatively charged liquid to clean the air by molecularly bonding to airborne pathogens in the air positively charged virus molecules. This same negatively charged liquid can also be used to destroy what is known as per- and poly-fluoroalkyl substances (PFAS) in water. PFAS contamination in water is a critical challenge the world is facing as PFAS have historically been extremely difficult to degrade with cost-effective, non-toxic, and efficient methods due to the very high strength of their carbon-fluorine bonds.

This negatively charged liquid may also be applied topically to a surface such as but not limited to, skin and other material that naturally grows, such as agriculture products or produce.

BACKGROUND

Researchers at the University of Michigan used a process known as cold plasma that uses electrostatic micro sparks to destroy airborne viruses. This process uses an electric powered negative ion generator, forced air system, and reactor. The way it works is that the air stream forces viruses into the reactor through a packed bed of electrostatically charged borosilicate glass beads. A high-voltage current generates micro sparks at each of the contact points. According to the researchers, viruses are inactivated by the micro sparks as they are carried through the spaces between the beads. A similar type of micro spark generating system has been used in the past that eliminates the need for external power, a reactor, or wires.

The Respiratory (Olfactory) System is made up of an array of positively charged sensors that, like an aircraft in flight, become more positively charged by air friction as air flows through the nasal passage. The sense of smell works by attracting the lesser charged fragrance molecules in the air to positively charged receptors on the inside walls of airways that are constantly being recharged. When the fragrance molecules reach these receptors, an electric impulse is sent to the brain that, in turn, interprets the information.

SUMMARY

The embodiments relate to systems and methods of targeted entity degradation, such as when the targeted entity may comprise one or more pathogens, PFAS, pests, compounds, or substances.

An aspect of the embodiments includes a method that includes forming anionic polymer encapsulants (CAPs) including fluid ingredients in a plasma reaction chamber (PRC) that comprises an outer dielectric polymer shell around the PRC. The fluid ingredients include at least one of: a) one or more essential oils; and b) an energy amplifying liquid. The method includes creating a plasma gas in the PRC, in response to a pulsed electromagnetic energy field, and forming cold plasma by discharging dielectric barrier plasma discharges (DBPDs) generated via the creation of the plasma gas from the PRC into a fluid medium having one or more targeted entities dispersed therein.

An aspect of the embodiments includes a system for targeted entity degradation that comprises anionic polymer encapsulants (CAPs) including fluid ingredients in a plasma reaction chamber (PRC) comprising an outer dielectric polymer shell around the PRC. The fluid ingredients include at least one of: a) one or more essential oils; and b) an energy amplifying liquid. The PRC comprises conductive whiskers which when exposed to a pulsed electromagnetic energy field release electrons that vaporize at least a portion of the fluid ingredients to create a plasma gas in the PRC. Cold plasma is formed by discharging dielectric barrier plasma discharges (DBPDs) generated via the creation of the plasma gas from the PRC into a fluid medium having one or more targeted entities dispersed therein.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3A illustrates an apparatus with nanotubes;

FIG. 3B illustrates a system with the apparatus of FIG. 3A filled or saturated with polymer encapsulants;

DETAILED DESCRIPTION

Figure 1:
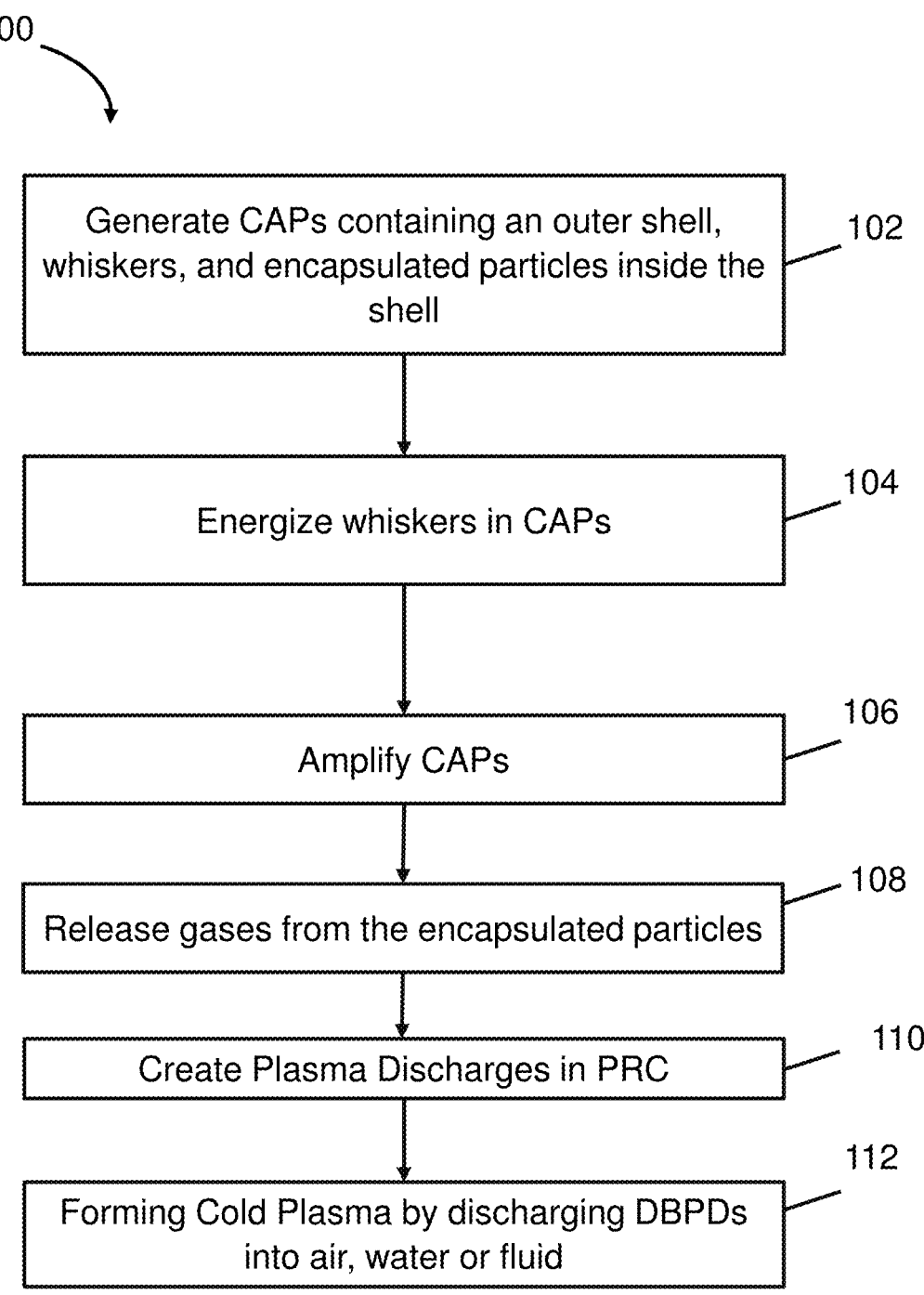
FIG. 1 illustrates a flowchart of a method for targeted entity degradation.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

FIG. 1 illustrates a flowchart of a method 100 for targeted entity degradation. The method steps may be performed in the order shown or a different order. One or more method steps may be added. One or more method steps may be performed contemporaneously. In some iterations, one or more method steps may be omitted. The method 100 will be described in combination with FIG. 2A that illustrates a polymer encapsulant (CAP) 200 in a pulsed electromagnetic energy field.

The method 100 may include (at 102) generating anionic polymer encapsulants (CAPs) 200, each CAP 200 includes a fluid 225 (e.g., essential oil, essential oil gas, etc.) encapsulated in an outer shell 210. The outer shell 210 may be an epoxy polymer shell. The polymer shell is made up of epoxy, PVC polymers, PVC co-polymers, or a combination thereof. The CAP 200 may be a porous particle.

The method 100 may include (at 104) energizing metal whiskers 220 in the CAPs 200, and as a result electrons are released. The method 100 may include (at 106) amplifying the CAPs, as will be described in relation to FIGS. 3A-3B. The method 100 may include (at 108) releasing gases from encapsulated fluids 225 (e.g., essential oil, essential oil gas, etc.). The method 100 may include (at 110) creating plasma discharges (or a plasma gas wherein these terms may be used interchangeably) in a plasma reaction chamber (PRC) 215. The method 100 may include (at 112) forming cold plasma by discharging dielectric barrier-plasma discharges (DBPDs) from the PRC 215 into air, water, fluid, and/or aqueous solution, as will be described in relation to FIG. 4. Air, water, fluid, and/or an aqueous solution may sometimes be referred to as a "fluid medium" which may have one or more pathogens, PFAS, pests (e.g., insects or rodents), undesirable compounds or substances (e.g., corrosion), or other targeted entities dispersed therein. The method is continuous or repeated for a period of time, such as a few seconds, minutes, to hours.

When nano-size metal whiskers 220 are exposed to pulsed electromagnetic energy, electrons are released at high temperatures from the energized metal whiskers. These electrons create "streamers" of electrons in the surrounding fluid 225 having essential oils. (Think of it as the same type of streamers that are created as the trail of bubbles seen when a bullet is fired into water.) These high temperature electron streamers vaporize the essential oils creating a plasma gas. The high temperatures generally associated with plasma are mitigated by the larger volume of essential oils. Hence the name cold (atmospheric) plasma. This all occurs inside of the dielectric (electrically insulating) polymer reaction chamber (PRC) 215.

The dielectric polymer shell is made up of a combination of negatively chargeable polymers that pick up a negative charge as a result of the internal reaction described above. Because they are all negatively charged, forcing them together generates energy (similar to the repulsion force experienced by bringing like faces of magnets together). Because these are insulated (dielectric), bringing these charged dielectric polymer particles together creates a what is known as a DBPD.

When DBPD reactions occurs in air, they create micro shocks when the charging energy is from a pulsed electromagnetic energy field. These same DBPD reactions in water create plasma activated water (PAW).

Referring again to FIG. 2A, the CAP 200 is generated by a polymer encapsulation process 205. An example method of forming an activated polymer encapsulant is described in U.S. Pat. No. 6,596,204, entitled "Method of Encapsulating a Volatile Liquid," which is incorporated herein by reference in its entirety. By way of non-limiting example, a fluid such as a liquid is encapsulated into a porous particle, such as a porous ceramic, having a resin cured with a catalyst shell (i.e., outer shell 210) surrounding a porous bead portion 212. The porous particle (i.e., CAP 200) is saturated with a fluid or liquid having an epoxy or other catalyst mixed therein so that when a resin is added to the saturated particles, the catalyst reacts with the resin only on the surface of each particle to harden a shell on the surface of the particle encapsulating the liquid in the particle. The catalyst is selected to include one or more metals that form the whiskers 220.

Figures 2A, 2B:
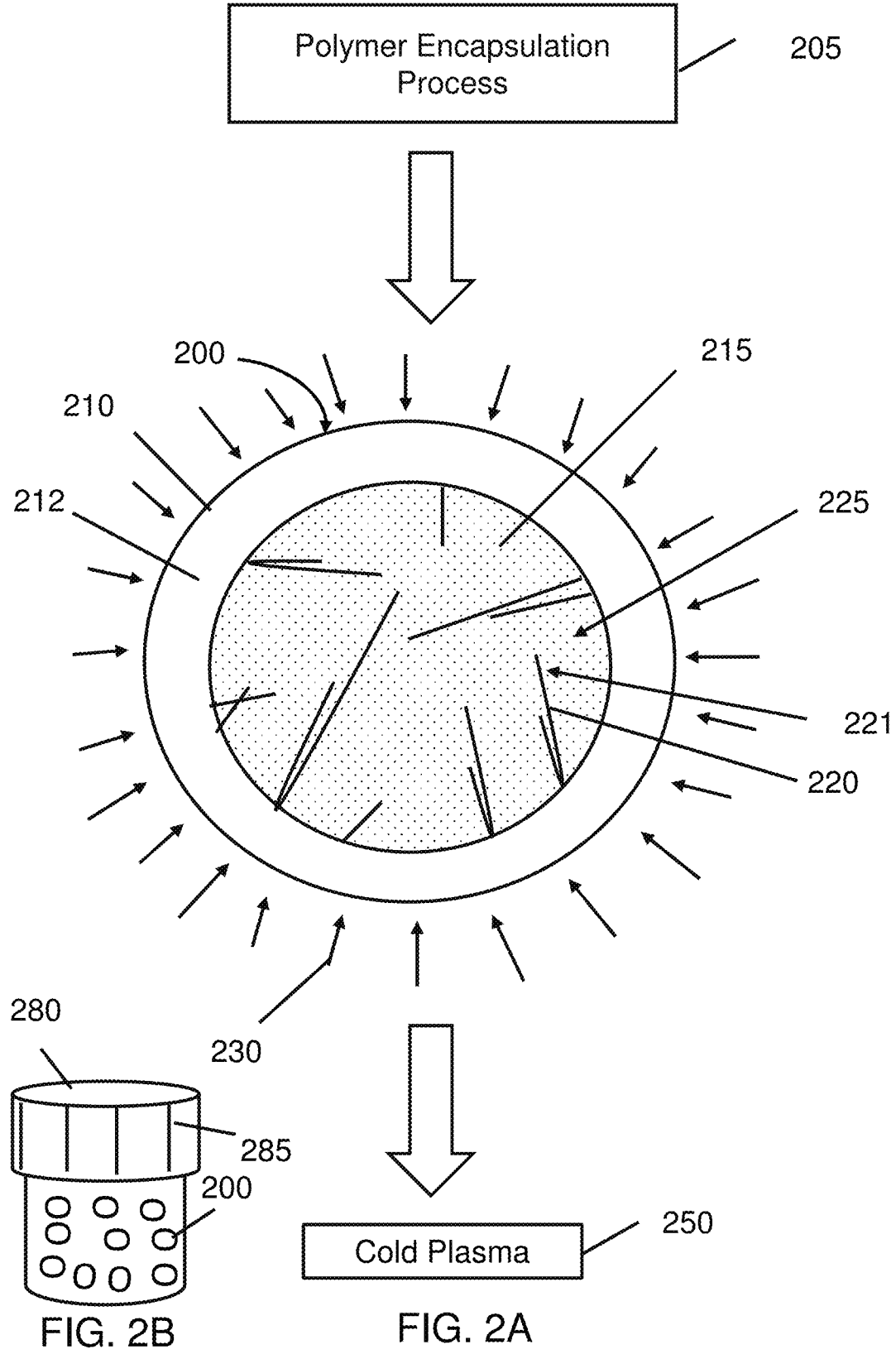
FIG. 2A illustrates a polymer encapsulant in a pulsed electromagnetic energy field.
FIG. 2B illustrates a container with a supply of polymer encapsulants.

FIG. 2B illustrates a container 280 having a supply of polymer encapsulants (i.e., CAPs 200) stored. The container 280 may include a removable lid 285. The container may be made of glass or a plastic, for example. The CAP 200 includes an outer shell 210 configured to form a plasma reaction chamber (PRC) 215 having conductive (metal) whiskers 220, each whisker 220 has a conductive tip 221. At least some of the whiskers 220 may radiate from an interior surface of the outer shell 210 and into the PRC 215. The whiskers 220 may include disparate metals, such as, Tin (Sn), copper (Cu), zinc (Zn), silver (Ag) and lithium (Li), for example. Lithium whiskers may be known as Dendrites. The metals that may be used to cure the polymer are Tin, Copper, Lithium, and Zinc. Depending on the combination of polymers used, percentages of each range from 0.01% to as much as 5%.

The whiskers 220 may be a fraction of a size of human hair. For example, the whiskers 220 may be nano-sized.

The remaining volume of space in the PRC 215 may be essentially filled with fluid 225 which is encapsulated by the outer shell 210. Some amount of air may be in the PRC 215. Thus, the whiskers 220 are submerged with the encapsulated fluid 225. The encapsulated fluid 225 may include submicron sized particles. The outer shell 210 of the CAP 200 is shown with arrows 230 impinging on the outer surface of the shell 210. The arrows 230 denote a pulsed electromagnetic energy field (hereinafter sometimes referred to as "electromagnetic pulses 230"). The inventor has determined that when the CAP 200 is in a pulsed electromagnetic energy field, a corona discharge occurs at the conductive tip 221 of one or more whiskers 220. Before discussing the corona discharge, the amplification process, at 106 of FIG. 1, will now be described.

FIG. 3A illustrates an apparatus 300A with nanotubes 310. The apparatus 300A may include a body 310 made of diatomaceous earth, for example. The body 310 may include nanotubes 320. Although the illustration of FIG. 3A illustrates a box-shaped apparatus 300A, the shape of the apparatus 300A is not limited to such shape. Instead, other three-dimensional structures may be used, including without limitation, a disc shaped structure, triangularly shaped structure, or any other shape provided they include tubes or other fibers that can be saturated with an amount of CAPs 200. The diatomaceous earth may include porous shells with nano-sized pathways. The shells may be found in nature or, alternately, manufactured. In some embodiments, diatomaceous earth may be substituted with other materials such as, without limitation, a fabric such as a fibrous fabric that is configured to hold the CAPs. It must be noted that the method 100 described herein may be performed irrespective of particle size (from sub-micron to macro).

The embodiments herein may use clay nanotubes filled with the CAPs 200.

FIG. 3B illustrates a system 300B having the apparatus 300A of FIG. 3A, filled or saturated with CAPs 200 (FIG. 2A). For amplification, when these passively charged encapsulated particles (i.e., CAPs 200) are brought together they form a plasma bed reactor (PBR) 325. (This is in contrast to a Packed Bed Reactor referred to by the University of Michigan that is formed by applying an external high voltage to a bed of borosilicate glass beads.) The apparatus 300A is filled with an amount of CAPs 200 which may be stored in a different container to prevent the CAPs 200 from being energized. For example, the CAPs 200 may be stored in a container which limits energizing by the CAPs until ready for use or added to the structure 300A.

Assume that the system 300B is now placed in air. The PBR 325 generated by pulsed electromagnetic energy field in air generates micro shocks 345. However, the PBR 325 may occur inside of the apparatus 300A and outside of the apparatus 300A where micro shock 345 are created. To eliminate crowding in the drawing, only the micro shocks 345 created in air are shown. However, it should be understood that since air permeates, the PBR 325 inside of the apparatus 300A also creates micro shocks 345.

When pulsed electromagnetic energy is used as a propellent, micro shocks 345 of Cold Plasma Negative Ions are released. These negatively charged ions can be used with conventional room diffusers to clean the air of particulate matter and pathogens, including viruses. They can also be used with antiviral essential oils to boost the immune system.

The metal whiskers 221 inductively (passively) harvest the necessary energy, and the fluid ingredient (e.g., essential oil(s)) provides a gas for energizing the encapsulated fluid 225 inside of the PRC 215. Essential Oils used are aromatic terpenes and up primarily of Oxygen (O), Nitrogen (N), and/or Carbon dioxide (CO2). This is important as these are the noble gasses that can produce the cold plasma. Additionally, the CAP 200 itself may pick up an electrical charge.

The effects of the pulsed electromagnetic energy field, denoted by arrows 230 of FIG. 2A, is amplified further at the nano-particle level by filling nanotubes with the CAPs 200. In various embodiments, the fluid or liquid in the CAPs 200 may have an energy amplifying liquid such as, without limitation (e.g., aloe vera and/or other plant-based liquids known to amplify negative air ions (NAI's) in the presence of pulsed electromagnetic energy fields). The energy amplifying liquid may include an energy amplifying essential oil such as, without limitations, Ravensara or other known essential oils.

The ingredients of the fluid 225 in the CAPs 200 may include at least one of: a) one or more essential oils; and b) an energy amplifying liquid, all of which are encapsulated in an electro-static activated polymer. The energy amplifying liquid amplifies the energy of the negative ions of the CAP 200 and/or other ingredients.

An example method of forming an activated polymer is described in U.S. Pat. No. 6,596,204, entitled "Method of Encapsulating a Volatile Liquid," which is incorporated herein by reference in its entirety.

The one or more essential oils in the fluid 225 may be selected from a list of terpene-based, oxygenated, aromatic essential oils that are known for their immune system boosting ability in the human body. Example essential oils may include frankincense and myrrh. Other terpene-based aromatic essential oils may include lemon oil, wild orange, dill oil, rosemary oil, *melaleuca* oil, and cypress oil. The lists of terpene-based aromatic essential oils may include fennel oil, black pepper oil, lime oil, and grapefruit oil, for example.

The ingredients in the fluid 225 may include *eucalyptus* oil, tea tree oil, sage oil, and moringa oil. These particular oils may be energy amplifying.

In some embodiments, the ingredients of the fluid 225 may include aloe vera, for example, without an essential oil. The pulsed electromagnetic energy is harvested at the nano-particle level by exposing porous particles (i.e., CAP 200) containing an anionic reactive polymer to the pulsed electromagnetic energy field generated by the human central nervous system and other sources.

In some embodiments, the ingredients of the fluid 225 may include photo-activated catalytic dyes that are known to kill human pathogens. Each when activated by a specific range of frequencies of the electromagnetic frequency spectrum is known to kill viruses and may include certain metal-based ions including, but not limited to, copper (Cu) and zinc (Zn) that are known to kill human pathogens on contact.

Hyaluronic Acid (HA) incorporated into water is known to penetrate the skin. In some embodiments, the HA is blended with micron-size CAPs (0.01%-1.5%, optimally 0.1%). The CAPs can be become packed into a confined space between the layers of skin. This packing action may form a PBR that amplifies the energy of the CAPs by bringing microscopic negatively charged particles together and forms cold plasma. The HA and CAPs solution may be stored in a container such as container 280 until ready for use, such as, for example and not limitation, in the form of a cream.

Figure 5:
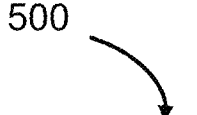
FIG. 5 illustrates a system including a transdermal patch.
Figure 5:
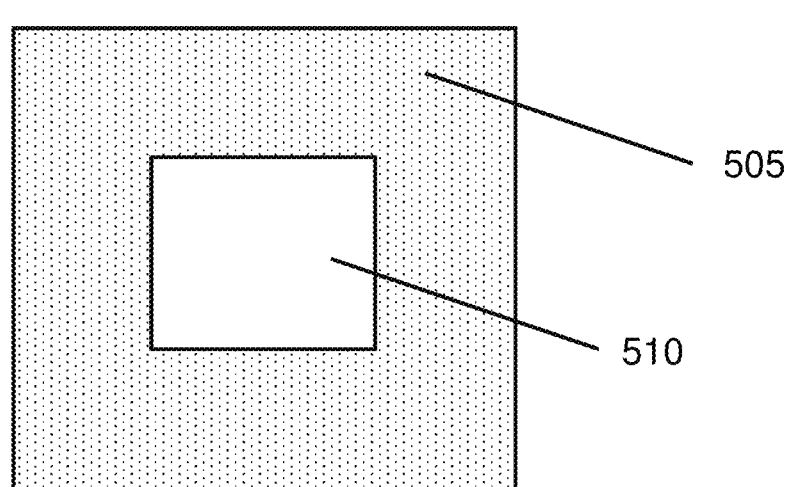

FIG. 5 illustrates a system 500 including a transdermal patch 505. The patch 505 includes on one side a skin adhesive, denoted by the dotted hatching. The patch 505 has an apparatus 510 that includes a structure, such as a fabric, and an amount of the solution of HA and CAPs saturating the structure. By way of non-limiting example, an amount of CAPs or a solution of HA and CAPs may saturate a transdermal patch or gauze fabric and fastened to the skin of a user. The gauze fabric may include an amount of solution or CAPs and fastened to the user's anatomy such as at a location on an upper or lower extremity, such as tape, body wraps, self-adhering body wraps, bands, or the like.

Referring again to FIGS. 1 and 2A, cold plasma 250 is generated by discharging, in response to a plasma reaction, DBPDs denoted by triangles 340 (FIG. 3B) that occur by a reaction inside of the PRC 215 with fluid 225. The plasma reaction may occur inside of the apparatus 300A and DBPD 340 may occur outside of the apparatus 300A.

The inventor has determined that pulsed electromagnetic energy fields create low voltage micro shocks 345 in a majority of encapsulated particles to recreate a reaction that effectuates a discharge of DBPDs. By way of non-limiting examples, the pulsed electromagnetic energy field is generated by a range of pulsed frequencies (e.g., Electrical Devices and Power Lines at 60 Hertz (Hz), Cell Phones and Cell Phone Towers at Gigahertz (GHz) levels, satellite transmissions (at, for example, 6 GHZ), and the Human Body). This pulsed electromagnetic energy field may be used to activate photocatalysts inside each CAP 200. A corona discharge may also be brought on by the ionization of air, or other fluid, surrounding a conductor that is electrically charged.

These CAPs 200 uses passive energy using inductive harvesting. For example, the CAP 200 may be powered by harvesting electromagnetic energy from the environment, by way of non-limiting example, denoted by arrows 230 (FIG. 2A). By combining this electromagnetic energy with oxygen molecules, for example, from essential oils of CAPs 200, a negative ion essential oil energy cell, called cold plasma, is created. The generated micro shocks as harvested energy continues to feed the electro-chemical reaction inside and outside of the CAP 200.

Cold Plasma, as defined in this disclosure, is a low temperature plasma that generates ions, chemically reactive atoms and/or molecules and/or ultraviolet (UV)-photons. In this case, the ions are negative air ions (NAI's) that are generated by an electro-chemical polymer reaction. More specifically, they are generated by a Lewis Acid/Base polymer reaction that uses terpenes found in aromatic essential oils as the oxygen molecule source and is fueled by pulsed electromagnetic energy that is harvested from pulsed electromagnetic field sources. This polymer reaction is described in U.S. Pat. No. 10,045,528, entitled "Method for Treating and Preserving Wood," which is incorporated herein by reference in its entirety, where porous particles are imbued with a plurality of essential oils and then micro-encapsulated in an epoxy-polymer shell.

In some embodiments, a negatively charged liquid that when diffused, uses the principal of molecular bonding to bond to positively charged virus molecules such as the corona virus to clean the air by killing airborne pathogens in the air on contact or when applied topically disburses the above-described electrostatic active liquid across conductive skin or when inhaled, deposits and adheres a layer of the above-described negatively charged, pathogen killing, nanoparticles onto the positively charged walls of the lungs, air passageways, etc., of the respiratory system.

The methods described herein have application to generate micro discharges in air which create pulsed electrostatic energy that is known to kill human pathogens on contact.

Figure 4:
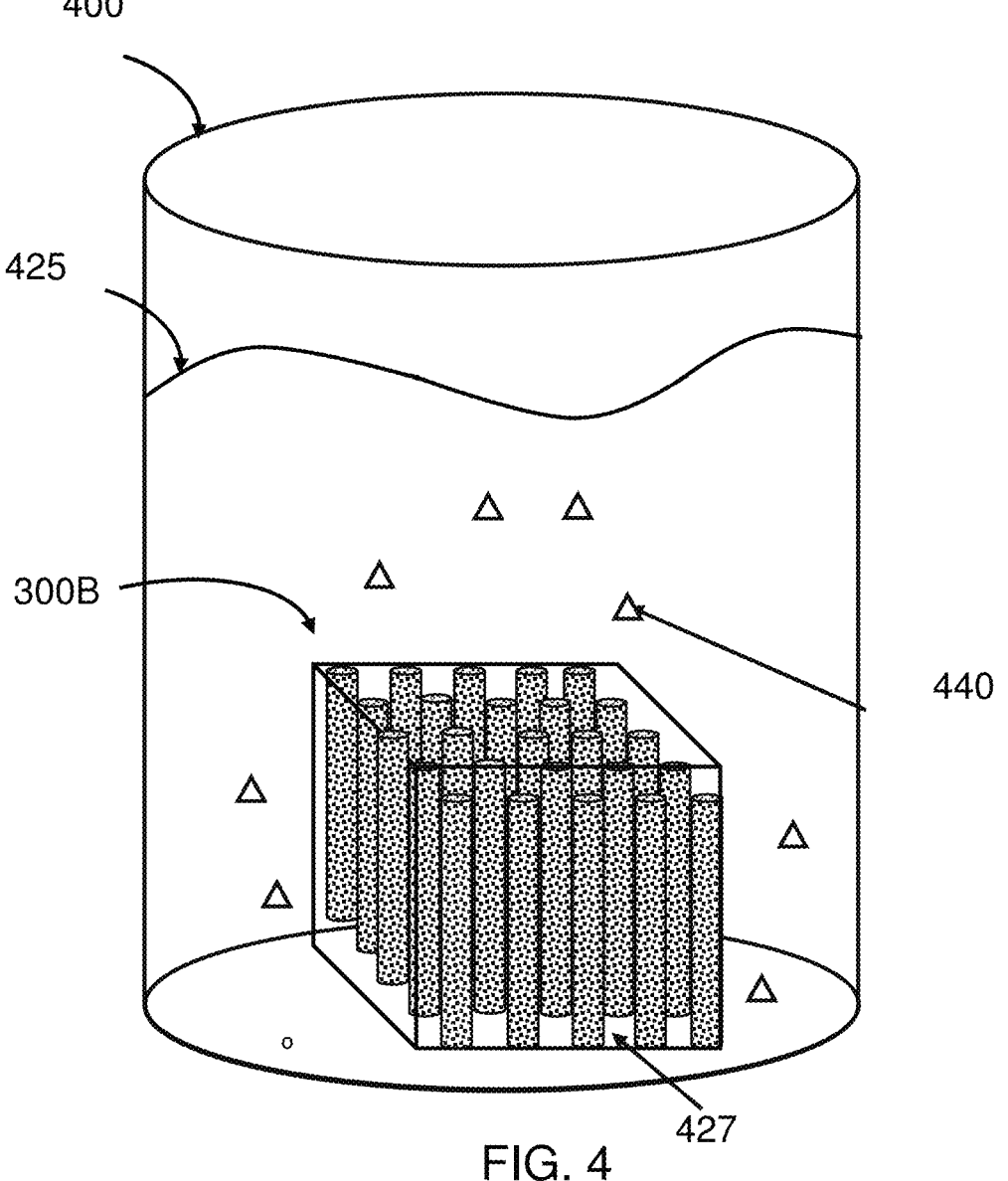
FIG. 4 illustrates the system of FIG. 3B installed in a container having water.

FIG. 4 illustrates the system 300B of FIG. 3B submerged in a container 400 filled with water 425. When the encapsulated particles (i.e., CAPs 200) are exposed to electromagnetic energy fields, plasma activated water (PAW) is generated by conductive needle-like fibers (i.e., whiskers 220) that extend outward into the PRC 215. These metal whiskers 220 significantly increase the intensity and concentration of the PAW that are diffused into the water 425. The PBR 427 generated by pulsed electromagnetic energy field in water generates the PAW. However, the PBR 427 may occur inside of the apparatus 300A and outside of the apparatus 300A cold plasma is formed by discharging dielectric barrier-plasma discharges (DBPDs) 440 into the water 425 to form the PAW.

When the encapsulated particles (i.e., CAPs 200) are discharged in the water 425, each CAP 200 may cluster 20-30 water molecules (this is according to NIH document "Negative Air Ions and their Effects on Human Health and Air Quality Improvement" (www.ncbi.nlm.nih.gov/pmc/articles/PMC6213340/pdf/ijms-19-02966.pdf, Section 5 page 7 incorporated herein by reference in its entirety). This clustering effect creates plasma activated water (PAW) inside container 400.

The pulsed electromagnetic energy 230 not only generates micro shocks, but it also migrates across the surface of a positively charged receptor through a process known as electromigration. One way to block a virus is to tie up the surfaces of the positively charged receptors by saturating them with negatively charged CAPs and/or the DBPD. This can be done simply by breathing air with CAPs filled with pleasant-smelling Essential Oil Negative Ion fragrance.

In some aspects, the cold plasma 250 generated via one or more CAPs 200 may be effective at hindering, destroying, removing, reducing, otherwise facilitating degradation of one or more targeted entities, such as PFAS, substances or compounds (e.g., corrosion), or pests (e.g., mosquitos, ticks, or rodents), as non-limiting examples. A supply of pulsed electromagnetic energy 230 may be available around most or all of the world via, for example, tens of thousands of satellites maintained in orbit around the Earth, offering use in a variety of applications and locations, similar to the ground energy transmission system envisioned by Nikola Tesla.

As a non-limiting illustrative example, the cold plasma 250 may be used to treat PFAS-contaminated water by breaking down the carbon-fluorine bonds within the PFAS molecules via the generation of highly reactive species within the cold plasma 250. This is due to the cold plasma 250 creating a high-energy environment with reactive species such as electrons, radicals, and ions that are able to directly attack and break down the carbon-fluorine bonds in the PFAS molecules with minimal production of harmful byproducts. Additionally, the temperature of the electron streamers released by the metal whiskers 220 may reach levels up to approximately 12,000 degrees Fahrenheit, and it has been observed that PFAS molecules break down at approximately 4,000 degrees Fahrenheit.

In some implementations, the CAPs 200 may be configured as a coating on one or more surfaces or elements susceptible to corrosion, such as, for example, steel. Maintenance of steel bridges, buildings, and other structures can be very expensive. By coating such structures with CAPs 200, the CAPs 200 may function similar to impressed current anodes to prevent or minimize the development of corrosion on the structures. As corrosion develops when electrons are lost, the CAPs 200 function to replace the electrons to reduce or prevent corrosion formation. In some aspects, the coating of CAPs 200 may include an amount of hyaluronic acid (HA).

In some embodiments, one or more CAPs 200 may be configured upon or at one or more strategic locations to hinder or deter pests from arriving or accumulating. As a non-limiting example, one or more portions of a street light may be coated with a plurality of CAPs 200 (and, in some aspects, HA) such that the cold plasma 250 generated by the CAPs 200 may deter insects such as moths from accumulating on the light, due to the inherent nature of the insects to resist and avoid electrical shocks. In some aspects, water from a lake or similar body of water may be pulled through piping, tubing, or a similar conduit (such as, for example and not limitation, polyvinyl chloride (PVC) piping) such that one or more CAPs 200 configured within, upon, or otherwise integrated with the piping or tubing may convert the received water into PAW. The PAW may be drawn through one or more Venturi tubes or similar apparatuses to generate a turbulent or vibrational effect within the PAW that generates an electromagnetic field by creating a dielectric barrier discharge (DBD), which creates the plasma, negatively charges the water that deters pests such as mosquitos. Hence, pests, which are positively charged will be repulsed by the DBD negatively charged aqueous fluid or water. In any embodiment disclosed herein, the aqueous fluid may be a part of another fluid.

In some aspects, PAW generated via one or more CAPs 200 may be useful in one or more various agricultural applications. The inventor has discovered, for example, that the germination period for corn may be reduced from an expected 7-15 days to approximately three days when watered with PAW. This has the potential to significantly increase the world's food supply, by offering multiple growing cycles in a season, as the CAPs 200 may be readily configured for use nearly anywhere on the planet. As used herein, targeted entities may also include agricultural items, such as seeds, plants, or produce. Furthermore, as used herein degradation with respect to agricultural applications may include removing impediments to allow for agricultural items to have accelerated growth by way of time and size.

In some embodiments, piping, tubing, or a similar conduit with or without faucet/spigot (such as, for example and not limitation, PVC piping), may be coated or integrated with a plurality of CAPs 200 and, in some aspects, an amount of HA, such that the PVC piping may be configured to convert an amount of water passing therethrough into PAW, thereby offering an on-demand supply of PAW from any adequate water source that may be used for applications such as, but not limited to, crop watering as well as cleansing activities.

The foregoing describes systems and methods for targeted entity degradation, such as, for example, destroying pathogens. However, the invention is not to be considered limited to the forms shown which are to be considered illustrative rather than restrictive.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

What is claimed is:

1. A method, the method comprising:
forming anionic polymer encapsulants (CAPs) including fluid ingredients in a plasma reaction chamber (PRC) comprising an outer dielectric shell around the PRC, the fluid ingredients include at least one of:
a) one or more essential oils, and
b) an energy amplifying liquid;
creating a plasma gas in the PRC, in response to a pulsed electromagnetic energy field; and
forming cold plasma by discharging dielectric barrier plasma discharges (DBPDs) generated via the creation of the plasma gas from the PRC into a fluid medium comprising one or more targeted entities.

2. The method of claim 1, wherein the energy amplifying liquid includes a plant-based fluid or an energy amplifying essential oil.

3. The method of claim 2, wherein the energy amplifying liquid comprises aloe vera or Ravensara.

4. The method of claim 1, further comprising amplifying the CAPs, prior to creating DBPDs.

5. The method of claim 4, wherein amplifying the CAPs includes filling a structure comprising nanotubes with an amount of the CAPs.

6. The method of claim 1, wherein the CAPs are passively charged by inductive harvesting of pulsed electromagnetic energy of the pulsed electromagnetic energy field in an environment.

7. The method of claim 1, further comprising creating a solution of hyaluronic acid (HA) and the CAPs.

8. The method of claim 7, further comprising applying the solution to skin of a wearer.

9. The method of claim 1, wherein the outer dielectric polymer shell of each CAP is formed of a catalyst including conductive whiskers radiating into the PRC.

10. The method of claim 9, wherein the conductive whiskers include at least one of tin, copper, zinc, silver, and lithium.

* * * * *